(12) United States Patent
Fu

(10) Patent No.: US 6,485,622 B1
(45) Date of Patent: *Nov. 26, 2002

(54) LITHIUM ION CONDUCTIVE GLASS-CERAMICS AND ELECTRIC CELLS AND GAS SENSORS USING THE SAME

(75) Inventor: Jie Fu, Sagamihara (JP)

(73) Assignee: Kabushiki Kaisha Ohara, Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/407,122

(22) Filed: Sep. 27, 1999

(51) Int. Cl.[7] ............... G01N 27/407; C03C 10/02; H01M 8/10
(52) U.S. Cl. ............. 204/421; 429/33; 429/319; 429/320; 429/322; 501/2; 501/4; 501/7; 501/8; 501/10; 501/46; 501/48; 501/73; 501/103; 501/152
(58) Field of Search .............. 501/2, 4, 7, 8, 501/10, 46, 48, 73, 78, 103, 152; 204/421–429; 429/33, 188, 304, 319, 320, 322

(56) References Cited

U.S. PATENT DOCUMENTS 5,702,995 A * 12/1997 Fu ............... 501/10

FOREIGN PATENT DOCUMENTS

| EP | 0838441 | 4/1998 |
|----|---------|--------|
| EP | 9857699 | 8/1998 |
| JP | 2302307 | * 12/1990 |

* cited by examiner

Primary Examiner—T. Tung
(74) Attorney, Agent, or Firm—Hedman & Costigan, P.C.

(57) ABSTRACT

Lithium ion conductive glass-ceramics comprise in mol %:

| $P_2O_5$ | 30–45% |
|---|---|
| $SiO_2$ | 0–15% |
| $GeO_2 + TiO_2$ | 25–50% |
| in which  $GeO_2$ | 0–50% |
| $TiO_2$ | 0–50% |
| $ZrO_2$ | 0–8% |
| $M_2O_3$ | 0<–10% | where M is an element or elements selected from the group consisting of In, Fe, Cr, Sc, Y, La, Ce, Pr, Nd, Sm, Eu, Gd, Th, Dy, Ho, Er, Tm, Yb and Lu

| $Al_2O_3$ | 0–12% |
|---|---|
| $Ga_2O_3$ | 0–12% |
| $Li_2O$ | 10–25% | and contain $Li_{1+X}(M, Al, Ga)_X(Ge_{1-Y}Ti_Y)_{2-X}(PO_4)_3$ (where $0<X\leq0.8$ and $0\leq Y\leq 1.0$) as a predominant crystal phase. A solid electrolyte, an electric cell and a gas sensor utilizing these glass-ceramics are also provided.

1 Claim, 2 Drawing Sheets

LITHIUM ION CONDUCTIVE GLASS-CERAMICS AND ELECTRIC CELLS AND GAS SENSORS USING THE SAME

BACKGROUND OF THE INVENTION

This invention relates to a lithium ion conductive glass-ceramics suitable for use as wholly solid electric cells, gas sensors and electrochemical devices of various types, and electric cells and gas sensors using such glass-ceramics.

Recent development in electronics has brought about high-performance electronic devices of a compact and light-weight design and, as a power source of such electronic devices, development of an electric cell of a high energy density and a long life is strongly desired for.

Lithium has the highest oxidation-reduction potential of $Li/Li^+$ of all metal elements and has the smallest mass per 1 mol and, therefore, a lithium cell can provide a higher energy density than other types of cells. Moreover, if a lithium ion conductive solid electrolyte is used, this electrolyte can be made very thin and, therefore, a cell of a thin film can be formed and increase in energy density per unit volume can thereby be realized.

A lithium ion cell which has been realized to date uses an organic electrolyte solution as its electrolyte and this makes it difficult to achieve a cell of a compact design such as a thin film design. This lithium ion cell has additional disadvantages that it has likelihood of leakage of electrolyte solution and likelihood of spontaneous combustion. If this lithium ion cell is replaced by a cell employing an inorganic solid electrolyte, a wholly solid cell of a high reliability will be realized.

Carbon dioxide gas produced by combustion of fossil fuel is a main cause of a hothouse effect which has recently become a serious problem and it has become necessary to incessantly watch the concentration of carbon dioxide gas. Therefore, establishment of a system for detecting carbon dioxide gas is a matter of increasing importance for the maintenance of a comfortable life in the future human society.

Carbon dioxide gas detection systems which are currently in use are generally of a type utilizing absorption of infrared ray. These systems, however, are large and costly and besides are susceptible to contamination. For these reasons, studies have recently been actively made to develop a compact carbon dioxide gas sensor using a solid electrolyte. Particularly, many reports have been made about studies using a lithium ion solid electrolyte.

For realizing such gas sensor using solid electrolyte, development of a solid electrolyte which is highly conductive, chemically stable and sufficiently heat proof is indispensable.

Among known electrolytes, $Li_3N$ single crystal (Applied Physics Letters, 30(1977) P621-22), $LiI—Li_2S—P_2S_5$ (Solid State Ionics, 5(1981) P663), $LiI—Li_2S—SiS_4$ (J. Solid State Chem. 69(1987) P252) and $LiI—Li_2S—B_2S_3$ (Mat. Res. Bull., 18(1983) 189) glasses have high conductivity of $10^{-3}$ S/cm or over at room temperature. These materials, however, have the disadvantage that preparation of these materials is difficult and these materials are not chemically stable and not sufficiently heat proof. Particularly, these materials have the fatal disadvantage that decomposition voltage of these materials is so low that, when they are used for an electrolyte of a solid cell, a sufficiently high terminal voltage cannot be obtained.

An oxide lithium solid electrolyte does not have the above described disadvantages and has a decomposition voltage which is higher than 3V and, therefore, it has possibility of usage as a wholly solid lithium cell if it exhibits a high conductivity at room temperature. It is known in the art that conductivity in an oxide glass can be increased by increasing lithium ion concentration. However, there is limitation in increasing the lithium ion concentration even if rapid quenching is employed for glass formation and conductivity of this glass at room temperature is below $10^{-6}$ S/cm at the highest.

Japanese Patent Application Laid-open Publication No. Hei 8-239218 discloses a gas sensor using a thin film of a lithium ion conductive glass. The conductivity of this lithium ion conductive glass thin film is within a range from $1.7 \times 10^{-7}$ S/cm to $6.1 \times 10^{-7}$ S/cm. This is not a sufficiently high value and a solid electrolyte having a higher conductivity is desired for.

There are many reports about oxide ceramics (sintered products) having a high conductivity. For example, $Li_4GeO_4—Li_3VO_4$ exhibits conductivity of $4 \times 10^{-5}$ S/cm at room temperature (Mat. Res. Bull. 15(1980) P1661), and $Li_{1+x}Al_xGe_{2-x}(PO_4)_3$ exhibits conductivity of $1.3 \times 10^{-4}$ S/cm at room temperature (Proceedings of 8th International Meeting on Lithium Batteries, Jun. 6–21, 1996, Nagoya, Japan P316-317). Oxide ceramics are superior in conductivity to oxide glasses but have the disadvantages that they require a complicated and troublesome process for manufacturing and that they are difficult to form, particularly to a thin film.

In short, the prior art lithium ion solid electrolytes have the problems that they are either low in conductivity, hard to handle or hard to form to a compact design such as a thin film.

It is, therefore, an object of the invention to provide glass-ceramics which have solved these problems and exhibit a high lithium ion conductivity at room temperature.

It is another object of the invention to provide a lithium electric cell and a gas sensor of a high performance by utilizing such glass-ceramics.

SUMMARY OF THE INVENTION

As described above, ceramics exhibit conductivity of $10^{-4}$ S/cm or over at room temperature. These ceramics, however, have pores and a large grain boundary which cannot be eliminated completely and existence of these pores and grain boundary results in decrease in conductivity. If, therefore, glass-ceramics including the above crystal are provided, there will be no pores and the grain boundary will be improved and, as a result, a solid electrolyte having a higher conductivity is expected to be produced. Besides, glass-ceramics which share a feature of glass can be easily formed into various shapes including a thin film by utilizing this feature of glass. For these reasons, glass-ceramics are considered to have practical advantages over ceramics made by sintering.

As a result of studies and experiments made by the inventor of the present invention on the basis of the above described basic concept, the inventor has succeeded in obtaining glass-ceramics having a high lithium ion conductivity at room temperature by producing glasses including ingredients of $P_2O_5$, $SiO_2$, $GeO_2$, $TiO_2$, $ZrO_2$, $M_2O_3$ (where M is en element or elements selected from the group consisting of In, Fe, Cr, Sc, Y, La, Ce, Pr, Nd, Sm, Eu, Gd, Tb, Dy, Ho, Er, Tm, Yb and Lu), $Al_2O_3$, $Ga_2O_3$ and $Li_2O$ and causing a crystal phase of conductive crystal $Li_{1+x}$(M, Al, $Ga)_X(Ge_{1-Y}Ti_Y)_{2-X}(PO_4)_3$ (where $0<X\leq0.8$ and $0\leq Y\leq1.0$) to precipitate from the glasses by heat treating these glasses. The inventor has also found that a lithium electric cell and a gas sensor using the glass-ceramics exhibit excellent characteristics.

For achieving the above described objects of the invention, there are provided lithium ion conductive glass-ceramics comprising, in mol %:

| | |
|---|---|
| $P_2O_5$ | 30–45% |
| $SiO_2$ | 0–15% |
| $GeO_2 + TiO_2$ | 25–50% |
| in which $GeO_2$ | 0–50% |
| $TiO_2$ | 0–50% |
| $ZrO_2$ | 0–8% |
| $M_2O_3$ | 0<–10% | where M is an element or elements selected from the group consisting of In, Fe, Cr, Sc, Y, La, Ce, Pr, Nd, Sm, Eu, Gd, Tb, Dy, Ho, Er, Tm, Yb and Lu

| | |
|---|---|
| $Al_2O_3$ | 0–12% |
| $Ga_2O_3$ | 0–12% |
| $Li_2O$ | 10–25% | and containing $Li_{1+X}(M, Al, Ga)_X(Ge_{1-Y}Ti_Y)_{2-X}(PO_4)_3$ (where $0<X\leq0.8$ and $0\leq Y\leq1.0$) as a predominant crystal phase.

In one aspect of the invention, there is provided a solid electrolyte for a lithium electric cell using these lithium ion conductive glass-ceramics.

In another aspect of the invention, there is provided a solid electrolyte for a gas sensor using these lithium ion conductive glass-ceramics.

In another aspect of the invention, there is provided a lithium electric cell comprising a case, a negative electrode, a positive electrode ad a solid electrolyte, said negative electrode, positive electrode and solid electrolyte being disposed in the case in such a manner that the negative electrode opposes the positive electrode through the solid electrolyte wherein said solid electrolyte is made of lithium ion conductive glass-ceramics comprising in mol %:

| | |
|---|---|
| $P_2O_5$ | 30–45% |
| $SiO_2$ | 0–15% |
| $GeO_2 + TiO_2$ | 25–50% |
| in which $GeO_2$ | 0–50% |
| $TiO_2$ | 0–50% |
| $ZrO_2$ | 0–8% |
| $M_2O_3$ | 0<–10% | where M is an element or elements selected from the group consisting of In, Fe, Cr, Sc, Y, La, Ce, Pr, Nd, Sm, Eu, Gd, Tb, Dy, Ho, Er, Tm, Yb and Lu

| | |
|---|---|
| $Al_2O_3$ | 0–12% |
| $Ga_2O_3$ | 0–12% |
| $Li_2O$ | 10–25% | and containing $Li_{1+X}(M, Al, Ga)_X(Ge_{1-Y}Ti_Y)_{2-X}(PO_4)_3$ (where $0<X\leq0.8$ and $0\leq Y\leq1.0$) as a predominant crystal phase.

In still another aspect of the invention, there is provided a gas sensor comprising a case, a negative electrode, a positive electrode, a solid electrolyte and a layer for which an electromotive force corresponding to the concentration of the gas is produced between the two electrodes, a lead connected to the negative electrode and a lead connected to the positive electrode, said negative electrode, positive electrode and solid electrolyte being disposed in the case in such a manner that the negative electrode opposes the positive electrode through the solid electrolyte wherein said solid electrolyte is made of lithium ion conductive glass-ceramics comprising in mol %:

| | |
|---|---|
| $P_2O_5$ | 30–45% |
| $SiO_2$ | 0–15% |
| $GeO_2 + TiO_2$ | 25–50% |
| in which $GeO_2$ | 0–50% |
| $TiO_2$ | 0–50% |
| $ZrO_2$ | 0–8% |
| $M_2O_3$ | 0<–10% | where M is an element or elements selected from the group consisting of In, Fe, Cr, Sc, Y, La, Ce, Pr, Nd, Sm, Eu, Gd, Tb, Dy, Ho, Er, Tm, Yb and Lu

| | |
|---|---|
| $Al_2O_3$ | 0–12% |
| $Ga_2O_3$ | 0–12% |
| $Li_2O$ | 10–25% | and containing $Li_{1+X}(M, Al, Ga)_X(Ge_{1-Y}Ti_Y)_{2-X}(PO_4)_3$ (where $0<X\leq0.8$ and $0\leq Y\leq1.0$) as a predominant crystal phase.

DETAILED DESCRIPTION OF THE INVENTION

In the description to follow, the compositions of the glass-ceramics made according to the invention are expressed on the basis of compositions of oxides as in the base glasses. Reasons for selecting the above described content ranges of the respective ingredients and a method for manufacturing the glass-ceramics will now be described.

By melting and cooling the base glass having the above described composition and heat treating the glass to cause the crystal phase of $Li_{1+X}(M, Al, Ga)_X(Ge_{1-Y}Ti_Y)_{2-X}(PO_4)_3$ (where $0<X\leq0.8$ and $0\leq Y\leq1.0$) to precipitate, dense glass-ceramics exhibiting a high lithium ion conductivity at room temperature which was never attained in the prior art ceramics were obtained. It has been found that the same crystal phase can be precipitated also in a composition range outside of the above described composition ranges but the ratio of this crystal is so low that lithium ion conductivity of such glass-ceramic is not sufficiently high for a practical use.

Among the ingredients described above, the effect of $M_2O_3$ (where M is an element or elements selected from the group consisting of In, Fe, Cr, Sc, Y, La, Ce, Pr, Nd, Sm, Eu, Gd, Tb, Dy, Ho, Er, Tm, Yb and Lu) is particularly important. A three-part system of $P_2O_5$—$GeO_2$—$Li_2O$ which does not contain the $M_2O_3$ ingredient can be glassified but melting property and thermal stability of the glass are poor and conductivity of glass-ceramic obtained by heat treating this glass is a low one of $10^{-8}$ S/cm or below.

By adding the $M_2O_3$ ingredient, the melting property and thermal stability of the glass are significantly improved. Difference between Tx (crystallization temperature of glass)

and Tg (transition temperature of glass) is generally used for estimating thermal stability of the glass and the glass becomes more stabilized thermally as this difference becomes larger. As will be shown in Examples of the present invention, a result was obtained in which Tx–Tg increased from 54° C. to 110° C. by the addition of $M_2O_3$.

It has also been found, surprisingly, that conductivity of the glass-ceramics after heat treatment increases by one figure or over by the addition of $M_2O_3$. For obtaining an excellent conductivity, the amount of $M_2O_3$ should be 10% or less. If the amount of this ingredient exceeds 10%, melting property and thermal stability of the mother glass are reduced rather than increased and conductivity of the glass-ceramics after heat treatment is also reduced. A preferable range of the $M_2O_3$ ingredient is 0.1–8% and, a more preferable range thereof is 0.5–6%.

The $P_2O_5$ ingredient is an essential ingredient for forming glass and it is also an ingredient which forms the conductive crystal phase of the glass-ceramics. If the amount of this ingredient is below 30%, difficulty arises in vitrifying whereas if the amount of this ingredient exceeds 45%, the conductive crystal phase does not grow from the glass and desired characteristics cannot be achieved.

$GeO_2$ and/or $TiO_2$ contributes to forming of glass and is also an ingredient which forms the conductive crystal phase. In both the glass and glass-ceramics, the two ingredients can be substituted by each other at any ratio within a continuous range. For glassifying, either of these ingredients must be added and, for enabling the conductive crystal phase to grow as a predominant crystal phase from the glass and thereby achieving a high conductivity, the total amount of $GeO_2$ and $TiO_2$ must be within a range from 25% to 50%. A preferable range is 0–45% for $GeO_2$ and $TiO_2$ respectively and 25–45% for $GeO_2+TiO_2$. A more preferable range is 0–40% for $GeO_2$ and $TiO_2$ respectively and 28–40% for $GeO_2+TiO_2$.

The $Li_2O$ ingredient is an essential ingredient for providing $Li^+$ ion carrier and thereby realizing the lithium ion conductivity. An excellent conductivity can be provided by addition of this ingredient in the range from 10% to 25%.

$ZrO_2$ is effective in enhancing precipitation of the above described crystal phase. If the amount of this ingredient exceeds 8%, melting property and thermal stability of the base glass are significantly deteriorated and making of the glass thereby becomes difficult. The upper limit of this ingredient therefore is 8%. A preferable range is 6% or below and a more preferable range thereof is 5% or below.

$SiO_2$ is effective in increasing melting property and thermal stability of the base glass and forming solid solution of $Si^{4+}$ ion in the crystal phase and thereby improving the lithium ion conductivity. If, however, the amount of this ingredient exceeds 15%, conductivity is deteriorated rather than improved. The upper limit of this ingredient therefore is 15%. A preferable range of this ingredient is 13% or below and a more preferable range thereof is 10% or below.

$Al_2O_3$ and/or $Ga_2O_3$ are effective in improving melting property and thermal stability of the base glass and forming solid solution of $Al^{3+}$ and/or $Ga^{3+}$ ion in the crystal phase and thereby improving the lithium ion conductivity. If, however, the amount of each of these ingredients exceeds 12%, thermal stability of the glass is deteriorated rather than improved and conductivity of the glass-ceramics is also reduced. The upper limit of each of these ingredients therefore is 12%. A preferable range of each of these ingredients is 11% or below and a more preferable range thereof is 10% or below.

For improving melting property of the glass, $B_2O_3$, $As_2O_3$, $Sb_2O_3$, $Ta_2O_5$, CdO, PbO, MgO, CaO, SrO, BaO and ZnO may be optionally added. Each of these ingredients should be added in an amount not exceeding 5%. If the amount exceeds 5%, conductivity decreases with the amount of addition of these ingredients.

A method for manufacturing the lithium ion conductive glass-ceramics of the present invention will now be described.

Starting materials are weighed at a predetermined ratio and mixed uniformly and the mixed materials are put in a platinum crucible and heated and melted in an electric furnace. First, gas components coming from the raw materials are evaporated at 700° C. and then the temperature is raised to 1300° C. to 1450° C. and the materials are melted at this temperature for about one to two hours. Then, the melt is cast onto a stainless steel plate to form sheet glass. The resultant glass is subjected to heat treatment within a temperature range from 600° C. to 1000° C. for one to twenty four hours and lithium ion conductive glass-ceramics containing $Li_{1+X}(M, Al, Ga)_X(Ge_{1-Y}Ti_Y)_{2-X}(PO_4)_3$ (where M is an element or elements selected from the group consisting of In, Fe, Cr, Sc, Y, La, Ce, Pr, Nd, Sm, Eu, Gd, Tb, Dy, Ho, Er, Tm, Yb and Lu) as a predominant crystal phase and exhibiting a high lithium ion conductivity is thereby provided.

The glass-ceramics of the present invention can be manufactured also by the following method.

Starting materials are weighed at a predetermined ratio and mixed uniformly and the mixed materials are put in a platinum crucible and heated and melted in an electric furnace. First, gas components coming from the raw materials are evaporated at 700° C. and then the temperature is raised to 1300° C. to 1450° C. and the materials are melted at this temperature for about one to two hours. Then, the melt is cooled in water to produce glass. The resultant glass is crushed with a ball mill and passed through a sieve of 150 mesh to provide glass powder. The glass powder is press-formed and put in an electric furnace to be heated at 600° C. to 1200° C. for one to twenty four hours. Thus, glass-ceramics containing the above described crystal phase as a predominant crystal phase and having a high lithium ion conductivity are provided.

BRIEF DESCRIPTION OF THE DRAWINGS

In the accompanying drawings.

EXAMPLES

Figure 1:
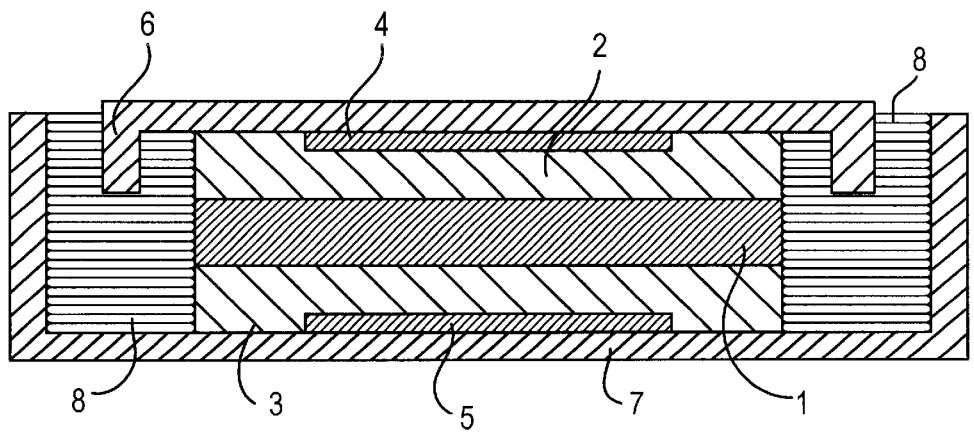
FIG. 1 is a sectional view of an example of a lithium cell using a lithium ion conductive solid electrolyte made of the glass-ceramic of Example 2.

Specific examples of the invention will be described below. It should be noted that these examples are illustrative only and the scope of the invention in no way is restricted by these examples.

Example 1

As starting materials, $NH_4H_2PO_4$, $GeO_2$, $Nd_2O_3$ and $Li_2CO_3$ were used. These materials were weighed to constitute a composition of 37.5% $P_2O_5$, 40% $GeO_2$, 5%$Nd_2O_3$ and 17.5% $Li_2O$ in mol %. The materials were mixed uniformly and then put in a platinum crucible and heated and melted in an electric furnace. First, $CO_2$, $NH_3$ and $H_2O$ coming from the raw materials were evaporated at 700° C. Then, the temperature was raised to 1350° C. and the raw materials were melted by heating them at this temperature for two hours. Thereafter, the melt was cast onto a preheated stainless steel plate to form a uniform sheet glass. The glass was annealed at 520° C. for four hours for removing thermal stress of the glass.

The glass thus produced was cut into specimens each having the size of 20 mm×20 mm. The glass specimens were polished on both surfaces and subjected to heat treatment at 680° C. for twelve hours and, as a result, a dense glass-ceramic was produced. The crystal phase which precipitated in the specimens was determined by the powder X-ray diffraction method. As a result, it was found that the precipitated crystal phase was $Li_{1-x}Nd_xGe_{2-x}(PO_4)_3$. This glass-ceramic exhibited a high conductivity of $2.0\times10^{-6}$ S/cm at room temperature.

Examples 2 to 7

Specimens of Examples 2 to 7 and Comparative Example 1 were prepared by employing a method similar to the one employed in preparing the glass-ceramic of Example 1. Compositions, conductivity at room temperature and Tx−Tg of the respective Examples and Comparative Example 1 are shown in Table 1. The conductivity of the glass-ceramics was measured within a range from $1\times10^{-2}$ Hz to $3\times10^{+7}$ Hz by the ac impedance. Resistance of the specimens (sum of grain resistance and grain boundary resistance) was determined from the Cole-Cole Plot and the conductivity was calculated by the equation $\sigma=(t/A)(1/R)$ (where $\sigma$ is conductivity, t is thickness of the specimen, A is electrode area and R is resistance of the specimen).

TABLE 1

| Example No. | 1 | 2 | 3 | 4 | 5 | 6 | 7 | Com. Ex. 1 |
|---|---|---|---|---|---|---|---|---|
| $P_2O_5$ | 37.5 | 37.5 | 37.5 | 37.5 | 37.5 | 37.5 | 37.5 | 37.5 |
| $GeO_2$ | 40.0 | 44.5 | 47.5 | 45.5 | 44.5 | 40.0 | 37.5 | 50.0 |
| $Al_2O_3$ | | | | | | | | 2.5 |
| $In_2O_3$ | | 3.0 | | | | | | |
| $Y_2O_3$ | | | 1.2 | 2.0 | | | | |
| $La_2O_3$ | | | | | | | 3.7 | |
| $Nd_2O_3$ | 5.0 | | | | | | | |
| $Gd_2O_3$ | | | | | | 5.0 | | |
| $Lu_2O_3$ | | | | | 3.0 | | | |
| $Li_2O_3$ | 17.5 | 15.0 | 13.8 | 15.0 | 15.0 | 17.5 | 18.8 | 12.5 |
| $T_x-T_g$(° C.) | 92 | 97 | 90 | 101 | 110 | 85 | 88 | 54 |
| Conductivty at room temperature (S/cm) | $2.0\times10^{-6}$ | $2.2\times10^{-6}$ | $1.0\times10^{-6}$ | $5.0\times10^{-7}$ | $1.2\times10^{-7}$ | $1.8\times10^{-6}$ | $1.4\times10^{-4}$ | $8.5\times10^{-9}$ |

From Table 1, Tx−Tg which indicates thermal stability of the glass is higher by 30° C. or more than the Comparative Example 1. It has also been found that conductivity at room temperature of the glass-ceramics is improved by one figure or more over the Comparative Example 1.

Example 8

As starting materials, $NH_4H_2PO_4$, $SiO_2$, $GeO_2$, $TiO_2$, $ZrO_2$, $Ga_2O_3$, $Cr_2O_3$, $Lu_2O_3$ and $Li_2CO_3$ were used. These materials were weighed to constitute a composition of 38% $P_2O_5$, 1% $SiO_2$, 18% $GeO_2$, 15% $TiO_2$, 2% $ZrO_2$, 6% $Ga_2O_3$, 1% $Cr_2O_3$, 2% $Lu_2O_3$ and 17% $Li_2O$ in mol %. The materials were mixed uniformly and then put in a platinum crucible and heated and melted in an electric furnace. First, $CO_2$, $NH_3$ and $H_2O$ coming from the raw materials were evaporated at 700° C. Then, the temperature was raised to 1450° C. and the raw materials were melted by heating them at this temperature for two hours. Thereafter, the melt was cast onto a preheated stainless steel plate to form a uniform sheet glass. The glass was annealed at 520° C. for four hours for removing thermal stress of the glass.

The glass thus produced was cut into specimens each having the size of 20 mm×20 mm. The glass specimens were polished on both surfaces and subjected to heat treatment at 850° C. for twelve hours and, as a result, a dense glass-ceramic was produced. The crystal phase which precipitated in the specimens was determined by the powder X-ray diffraction method. As a result, it was found that the precipitated crystal phase was $Li_{1+x}(Cr, Lu, Ga)_x(Ge_{1-Y}Ti_Y)_{2-x}(PO_4)_3$. This glass-ceramic exhibited a high conductivity of $3.0\times10^{-4}$ S/cm at room temperature.

Examples 9 to 12

Examples 9 to 12 were prepared by a method similar to the one employed in preparing the glass-ceramic of Example 8. Compositions and conductivity at room temperature of the respective Examples are described in Table 2. It will be understood that all compositions have conductivity of $10^{-4}$ S/cm or over.

TABLE 2

| Example No. | 8 | 9 | 10 | 11 | 12 |
|---|---|---|---|---|---|
| $P_2O_5$ | 38.0 | 32.2 | 33.5 | 35.0 | 39.0 |
| $SiO_2$ | 1.0 | 8.0 | 6.0 | 4.0 | |
| $GeO_2$ | 18.0 | 27.0 | 2.0 | 8.0 | 12.0 |
| $TiO_2$ | 15.0 | 10.0 | 40.0 | 35.0 | 26.0 |
| $ZrO_2$ | 2.0 | 4.0 | | | |
| $Al_2O_3$ | | 3.0 | | 4.5 | 4.0 |
| $Ga_2O_3$ | 6.0 | | 3.0 | | |
| $Fe_2O_3$ | | | | | 2.0 |
| $Cr_2O_3$ | 1.0 | | | | |
| $La_2O_3$ | | | 2.0 | | |
| $Nd_2O_3$ | | | | 1.0 | |
| $Gd_2O_3$ | | 1.0 | | | |
| $Er_2O_3$ | | 1.0 | | | |
| $Lu_2O_3$ | 2.0 | | | | |
| $Li_2O$ | 17.0 | 14.5 | 13.5 | 12.5 | 17.0 |
| Conductivity at room temperature (S/cm) | $3.0\times10^{-4}$ | $3.5\times10^{-4}$ | $4.2\times10^{-4}$ | $6.3\times10^{-4}$ | $7.2\times10^{-4}$ |

Example 13

As a typical example of a lithium electric cell, an example of flat type cell using the lithium ion conductive glass-ceramic of Example 2 as a solid electrolyte is shown in the sectional view of FIG. 1. The cell is composed of a negative electrode container 6, a negative electrode collector 4 constructed of a conductive thin film or a thin film made of aluminum or stainless steel, a negative electrode 2, a lithium ion conductive glass-ceramic layer 1, a positive electrode 3, a positive electrode collector 5 constructed of a conductive thin film or a thin film made of aluminum or stainless steel, a positive electrode container 7 and an insulating filler 8 made of an insulating material such as polypropylene. The positive and negative electrodes 2 and 3 are received in the case formed by the positive and negative electrode containers 6 and 7 in such a manner that these electrodes 2 and 3 oppose each other through the lithium ion conductive glass-ceramic layer 1. The positive electrode 3 is connected to the positive electrode container 7 through the positive electrode collector 5 and the negative electrode 2 is connected to the negative electrode container 6 through the negative electrode collector 4. Chemical energy produced in the cell can be collected as electric energy from terminals of the negative electrode container 6 and the positive electrode container 7.

In constructing the cell made according to the invention, various other materials which are conventionally used for forming a cell can be used except for the solid electrolyte portion.

The lithium ion conductive glass-ceramic layer must be sufficiently thin, i.e., 1 mm or less and preferably 0.5 mm or less. Many reports and proposals have been made about the material of the positive electrode 3 and it is typically made of $LiCoO_2$ or $Li_{1-x}V_3O_8$. Likewise, reports and proposals have been made about the material of the negative electrode 2 and it is typically made of $Li_4Ti_5O_{12}$ or carbon.

As to the positive and negative electrodes 2 and 3 formed on the opposite surfaces of the lithium ion conductive glass-ceramic layer 1 and the collectors 4 and 5 formed in the negative and positive electrodes 2 and 3, these component parts may be preformed respectively and stacked one after another to a composite cell. Alternatively, the positive and negative electrodes 2 and 3 and the collectors 4 and 5 may be formed sequentially by any of suitable known methods including ion spattering, CVD, screen printing, coating, sol-gel method, ion plating, ion beam evaporation and electron beam evaporation.

Figure 3:
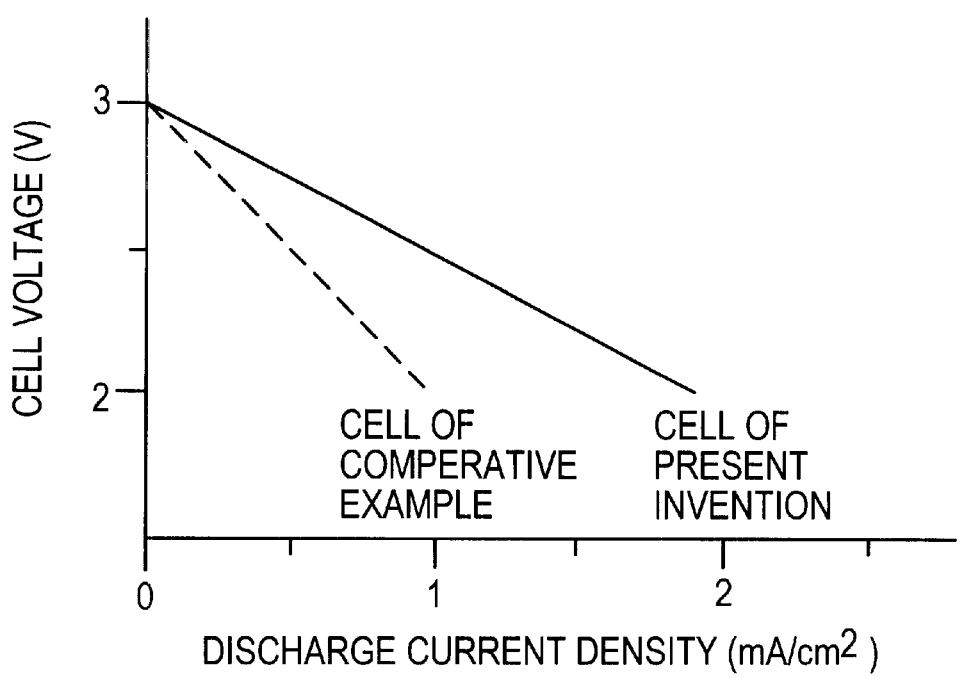
FIG. 3 is a graph showing an effective discharge characteristic of the cell shown in FIG. 1.

Effective discharge characteristics of this cell and a cell of a comparative example are shown in FIG. 3. As the comparative example, a cell is composed in the same manner as in the above example except that the solid electrolyte is formed by mixing 1.7 mol of titanium oxide, 0.7 mol of lithium carbonate, 3.0 mol of ammonium phosphate and 0.2 mol of aluminum oxide in an agate mortar, press-forming the mixture to pellets and sintering the pellets at 900° C. for two hours, crushing the sintered pellets again in an agate mortar, press-forming the crushed material which has passed a sieve of 400 mesh to pellets again, sintering the pellets at 1000° C. for two hours and processing the sintered pellets to a thin plate.

Example 14

Figure 2:
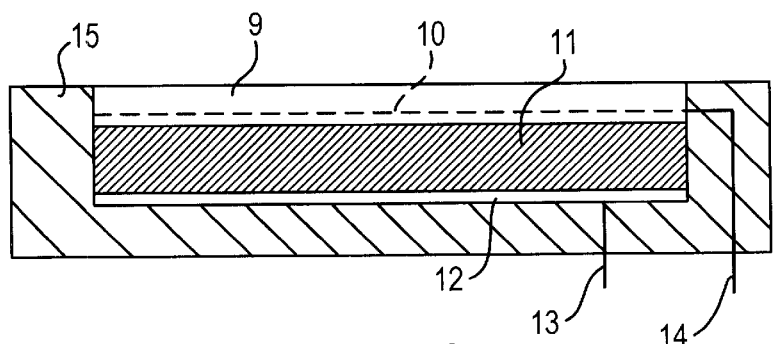
FIG. 2 is a sectional view of an example of a gas sensor using a lithium ion conductive solid electrolyte made of the glass-ceramic of Example 8.

As a typical example of a gas sensor, an example of a carbon dioxide gas sensor using the lithium ion conductive glass-ceramic of Example 8 as a solid electrolyte is shown in the sectional view of FIG. 2. The upper and lower surfaces of a lithium ion conductive glass-ceramic layer 11 are polished to provide the layer 11 having a thickness of 1 mm to 2 mm, preferably 1 mm or below and more preferably 0.5 mm or below. On one of the surfaces of the layer 11 (the upper surface in the illustrated example) is formed, by ion spattering, a layer 9 of metal carbonate, preferably lithium carbonate or a mixture of lithium carbonate and other carbonate. A platinum mesh to which a lead 14 is connected is disposed on the surface of this metal carbonate layer 9 to form an electrode 10. Then, the metal carbonate layer 9 is formed again on the upper surface of the electrode 10 to fix the electrode 10. On the other surface (the lower surface in the illustrated example) of the lithium ion conductive glass-ceramic layer 11 is formed, by evaporation, a platinum thin film to form an electrode 12. A lead 13 is connected to the electrode 12. These component parts are housed in a package 15. According to this sensor, an electromotive force corresponding to the concentration of carbon dioxide gas is produced between the two electrodes due to dissociation equilibrium of the carbonate by the carbon dioxide gas in a mixture gas including the carbon dioxide gas and, therefore, the concentration of the carbon dioxide gas can be detected by measuring this electromotive force.

Forming of the carbonate layer and the electrode layer is not limited to the above method but these layers may be formed by other known methods including CVD, screen printing, sol-gel method, ion plating, ion beam evaporation, MBE, vacuum evaporation and electron beam evaporation.

Figure 4:
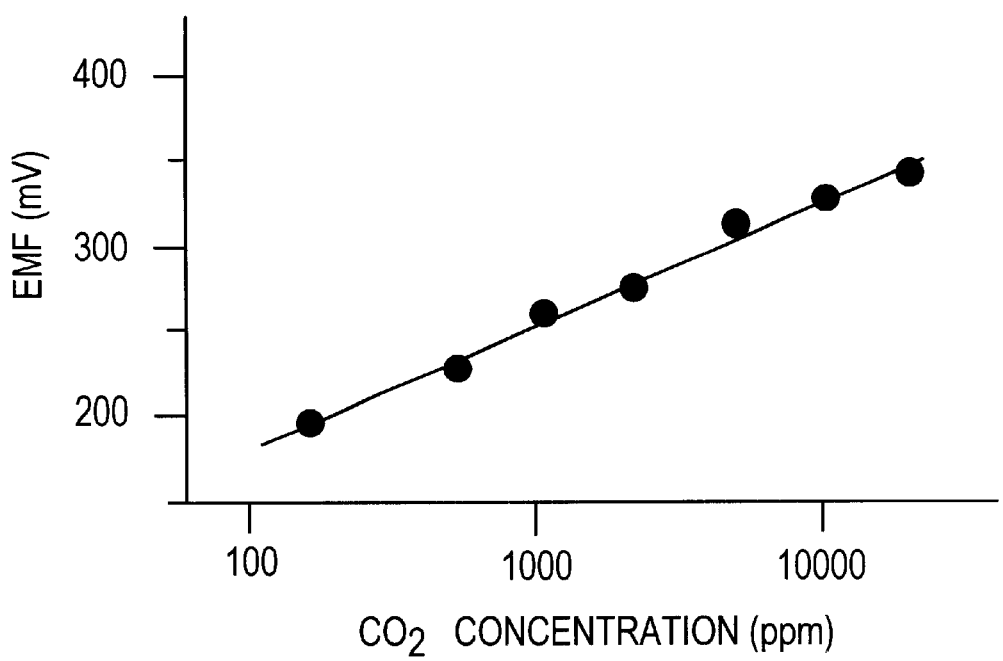
FIG. 4 is a graph showing an electromotive force characteristic by a carbonate gas partial pressure at room temperature of the gas sensor shown in FIG. 2.

The electromotive force characteristic by a carbonate gas partial pressure at room temperature of this gas sensor is shown in FIG. 4.

As described above, the lithium ion conductive glass-ceramics according to the invention have a very high lithium ion conductivity, are easy to manufacture and chemically and thermally stable and, therefore, these glass-ceramics can be utilized for various electrochemical devices including electric cells (including a fuel cell) and gas sensors.

What is claimed is:

1. Lithium ion conductive glass-ceramics comprising in mol %:

| | |
|---|---|
| $P_2O_5$ | 30–45% |
| $SiO_2$ | 0–15% |
| $GeO_2 + TiO_2$ | 25–50% |
| in which $GeO_2$ | 0–50% |
| $TiO_2$ | 0–50% |
| $ZrO_2$ | 0–8% |
| $M_2O_3$ | $0 < -10\%$ |
| $Al_2O_3$ | 0–12% |
| $Ga_2O_3$ | 0–12% |
| $Li_2O$ | 10–25% | and containing $Li_{1+x}(M, Al, Ga)_x(Ge_{1-y}Ti_y)_{2-x}(PO_4)_3$ (where $0 < X \leq 0.8$ and $0 \leq Y \leq 1.0$) as a predominant crystal phase, the glass ceramics being obtained by melting raw materials to a melt, casting the melt to a glass and subjecting the glass to a heat treatment, wherein M is an element selected from the group consisting of Nd, Sm, Eu, Gd, Tb, Dy, Ho, Er, Tm, and Yb.

* * * * *